United States Patent [19]

Lustig et al.

[11] 4,289,849
[45] Sep. 15, 1981

[54] TOOLS FOR DRILLING, REAMING AND THE LIKE WITH SIMULTANEOUS ANGULAR AND LINEAR OSCILLATORY MOTIONS

[75] Inventors: Leopold P. Lustig, 304 Greenwood St., Newton Ctr., Mass. 02159; Anselm Yaron, Brookline, Mass.

[73] Assignee: Leopold Paul Lustig, Newton, Mass.

[21] Appl. No.: 135,359

[22] Filed: Mar. 31, 1980

[51] Int. Cl.³ ............................................. A61C 00/07
[52] U.S. Cl. ........................................ 433/123; 74/50
[58] Field of Search ................ 433/118, 91, 122, 123; 74/50, 570, 750, 55

[56] References Cited

U.S. PATENT DOCUMENTS 1,711,846  5/1929  Heilborn .............................. 433/122

Primary Examiner—Robert Peshock
Attorney, Agent, or Firm—Alfred H. Rosen

[57] ABSTRACT

A dental contra-angle which supports a tool socket for combined motion consisting of two oscillatory movements simultaneously, one motion being a linear reciprocating motion parallel to the axis of rotation, and the other motion being an oscillatory motion around the axis of rotation. A tool receiving aperture opens through one end of the socket and extends along the axis toward the other end. A tool for treating a root canal, when installed in the socket, will be given a combined motion consisting simultaneously of a linear reciprocating motion in the axis of the root canal, and an angular oscillatory motion around the axis of the root canal. The resulting motion of such a tool is one of dipping with simultaneous partial rotation.

7 Claims, 4 Drawing Figures

U.S. Patent   Sep. 15, 1981   4,289,849
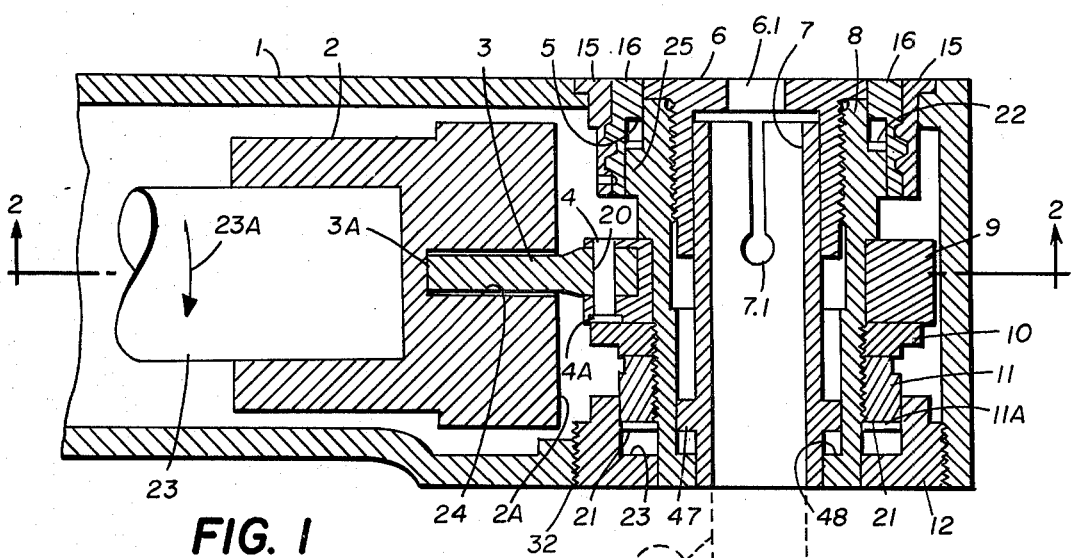
FIG. 1
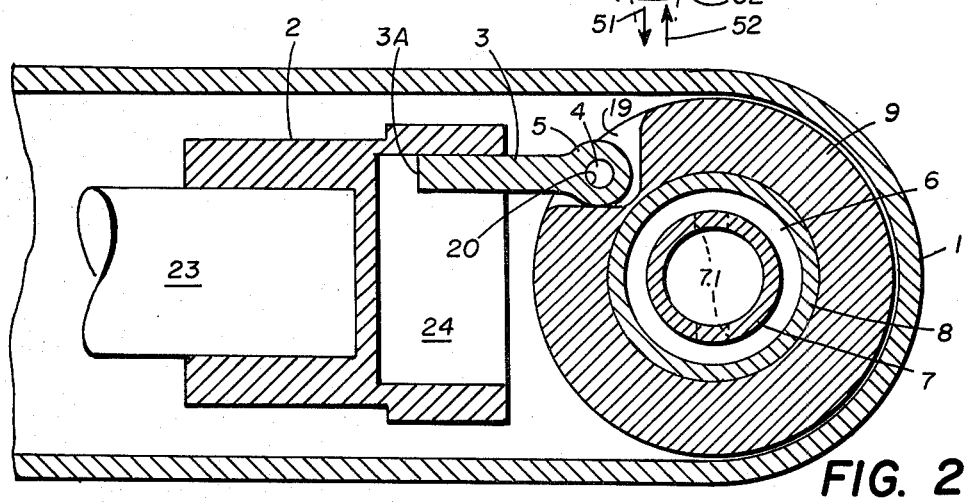
FIG. 2
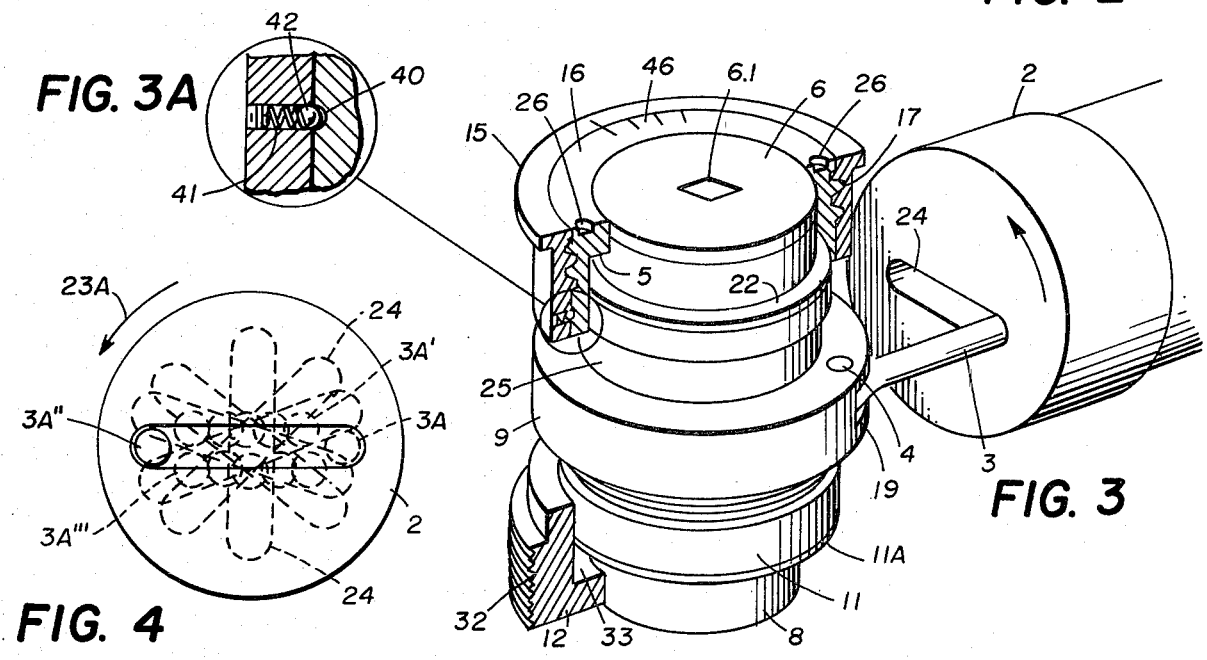
FIG. 3A
FIG. 3
FIG. 4

TOOLS FOR DRILLING, REAMING AND THE LIKE WITH SIMULTANEOUS ANGULAR AND LINEAR OSCILLATORY MOTIONS

INTRODUCTION

This invention relates in general to tools and instruments for drilling, boring, reaming and the like with a new combination of substantially simultaneous linear reciprocating motion and angular oscillatory motion, relative to the longitudinal axis of a tool or of the hole that is being bored or prepared. A dental instrument incorporating the invention is particularly suited for endodontic preparations; the invention is herein illustrated in connection with an endodontic contra-angle.

THE PRIOR ART

Within the immediately-past decade dental instruments have appeared which seek to mechanize the treatment of root canals. These instruments attempt to mimic the hand motions that are used by dentists when manipulating files, reamers and broaches in root canals. Examples are:

Garnier—U.S. Pat. No. 3,578,745—discloses an endodontic instrument rotatably supporting a tool socket while holding it against axial movement, with drive means for rotationally oscillating the socket about its longitudinal axis through a pre-determined angle.

Bassi et al—U.S. Pat. No. 3,747,216—discloses an endodontic instrument rotatably supporting a tool socket, with drive means for rotationally oscillating the socket about its longitudinal axis through a pre-determined angle while at the same time rotating the socket uniformly in one direction about its longitudinal axis. The socket is held against axial movement, but the tool is said to be threaded into a plug which does not rotate with the socket, so that the continuous rotary motion of the socket produces a uniform rectilinear motion of the tool parallel to the axis of rotation of the socket.

Nakanishi—U.S. Pat. No. 3,969,823—discloses an endodontic instrument rotatably supporting a tool socket with drive means for rotating the socket continuously in one direction while rectilinearly oscillating the socket in a direction parallel to its longitudinal axis.

Other patents showing tool holders for a reciprocating dental tool are Malata et al., U.S. Pat. No. 3,967,380; Greenberg, U.S. Pat. No. 2,328,270; and Lustig et al., 4,173,828.

GENERAL NATURE OF THE INVENTION

The present invention provides a new contra-angle which supports a tool socket for combined motion consisting of two oscillatory movements simultaneously, one motion being a linear reciprocating motion parallel to the axis of rotation, and the other motion being an oscillatory motion around the axis of rotation. A tool receiving aperture opens through one end of the socket and extends along the axis toward the other end. A tool can be held in any desired manner in the tool receiving aperture. A tool for treating a root canal, when installed in the socket, will be given a combined motion consisting simultaneously of a linear reciprocating motion in the axis of the root canal, and an angular oscillatory motion around the axis of the root canal. The resulting motion of such a tool is one of dipping with simultaneous partial rotation.

BRIEF DESCRIPTION OF THE DRAWINGS

FIG. 1 is a partial longitudinal section through a dental contra-angle made according to the invention;

FIG. 2 is a partial longitudinal section taken along line 2—2 in FIG. 1;

FIG. 3 is a partly broken-away isometric view of the contra-angle shown in FIGS. 1 and 2;

FIG. 3A is an exploded view of a detail of FIG. 3; and

FIG. 4 is a schematic illustration of the multi-directional drive mechanism shown in FIGS. 1-3.

DESCRIPTION OF THE ILLUSTRATED EMBODIMENT OF THE INVENTION

Referring to FIGS. 1-3, inclusive, a generally tubular contra-angle housing 1 encloses a drive shaft 23 on its longitudinal axis, the drive shaft being supported within the housing by usual supporting means that are not illustrated. It will be understood, also, that the housing 1 can be coupled to a dental engine by any of the known coupling systems, which not being part of the invention are likewise not illustrated. The drive shaft is adapted to be rotated on its longitudinal axis, as is represented by an arrow 23A. A hub 2 is fixed on the inner end of the drive shaft, for coupling with a pivot link 3 through a slot 24 extending diametrically across the face 2A of the hub, and extending a fixed depth into the hub, into which an arm 3A of the link 3 extends. The housing 1 mounts and supports a principal tool-operating sleeve 8 for two combined oscillatory motions relative to a tool axis A—A which extends transversely to the rotational axis of the drive shaft 23, one motion being a linear reciprocating motion in the axis A—A, as is indicated by a pair of straight arrows 51 and 52, and the other motion being an angular oscillatory motion around the axis A—A, as is indicated by a pair of curved arrows 61 and 62. The resulting motion of the sleeve 8 is one of dipping (in the direction of the axis A—A) with simultaneous partial rotation.

A ring 9 for pivotally receiving the link 3 is pressfitted to the exterior of the sleeve 8, about midway between the ends of the sleeve. A slot 19 in the ring 9, has a pair of opposing holes 20,20 to receive a pivot pin 4. The pivot link pin 3 has an eye-hole end 3B through which the pivot pin 4 extends parallel to the tool axis A—A, fixing the link 3 pivotally to the ring 9. The eye-hole end 3B of the link is snugly fitted between the arms of the slot 19, as is seen in FIG. 1, and can pivot about 90° around the pivot pin 4, as is seen in FIG. 2. Through the slot 24 in the hub 2, the link 3 and the ring 9, rotational motion of the drive shaft 23 is converted into the above-described combined oscillatory motions of the principal tool-operating sleeve 8.

The pivot pin 4 is held in position in the holes 20,20 by an internally-threaded hub 10 fixed on the exterior of the sleeve 8 and bearing against a head 4A of the pin; the nut 10 bears also against the ring 9. A second internally-threaded nut 11 is also fixed on the exterior of sleeve 8 and screwed tight against the first nut 10 at one side. The other, free, side 11A of the second nut is preferably covered with a first resilient annular piece 21. On the opposite side of the ring 9, the sleeve 8 has an annular boss 25, the shoulder of which farther removed from the ring 9 is covered with a second resilient annular piece 22. The resilient annular pieces are intended to cushion the stopping of the sleeve 8 in the limits of its linear reciprocating motion; they may be made of any suitable material, for example a plastics material. Since, as will become apparent, the sleeve 8 may be driven in rotational oscillation while it is engaged in a limit of its linear reciprocating motion, it is preferable that the resilient annular pieces 21, 22 shall be made of a low-friction material, for example Teflon (TM).

For holding the sleeve 8 in the housing 1, a first retaining nut 12 is screw-fitted into one side of the housing 1, and a second adjustable retaining nut assembly 15,16 is fitted into the opposite side of the housing. The first nut 12 has portions of smaller and larger diameters, respectively, separated by a shoulder 33. The sleeve 8 fits telescopically into the portion of smaller diameter; the second nut 11 fits telescopically into the portion of larger diameter; and the free side 11A of the second nut confronts the shoulder 13, which establishes one limit of linear reciprocating motion of the sleeve 8.

The second retaining nut assembly is in two parts 15,16 of which the first part 15 is affixed to the housing 1, preferably in a permanent manner. The second part 16 is threadedly engaged into the first part, preferably on a high angle acme thread 17 (FIG. 3) for permitting the making of small adjustments between the two parts in the direction of the tool axis A—A. The second part has a portion of smaller diameter into which the sleeve 8 fits telescopically and a portion of larger diameter into which the boss 25 fits telescopically. A shoulder 5 between these two portions confronts the shoulder of the boss 25 which bears the second resilient annular piece 22; this shoulder 5 establishes a second limit of linear reciprocating motion of the sleeve 8.

The distance between the limits of linear reciprocal motion of the sleeve 8 is adjustable by turning the second part 16 within the first part 15 of the second retaining nut assembly. For convenience, a pair of diametrically-opposed spanner holes 26 are provided in the outer end surface of the second part 16. To facilitate a quantitative adjustment vernier markings 46 may also be provided on the outer end surfaces of both parts 15,16. To provide fixed adjustment positions, a ball-detent assembly 40,41,42, as shown in FIG. 3A, may also be provided. With these conveniences, the distance between the limits of linear reciprocal motion can be adjusted in a manner somewhat similar to adjusting the focus of a small camera with click stops.

The principal tool-operating sleeve 8 can support any type of tool holder that is desired. For the purposes of illustrating the invention, a friction grip tool holder 7 is shown. The sleeve 8 is internally threaded at one end, (for convenience called the "upper end"), and receives in that end an externally-threaded cap 6 fitted with a socket hole 6.1. The tool holder 7 has a boss 47 which fits snugly inside the sleeve 8 and with the aid of a shoulder 48 on the lower end of the sleeve keeps the tool holder from falling out of the lower end of the sleeve. The cap 6 retains the tool holder at the upper end of the sleeve. The internal surface of the cap 6 is provided with a low cinical inclination (not shown), through which the slotted upper end of the tool holder can be compressed when the cap 6 is screwed into the sleeve 8. Tightening the cap 6 against the tool holder 7 in this manner provides gripping force to retain a tool 13 in the sleeve. The cap 6 can be tightened, and loosened, to retain or to release a tool, by use of a wrench suitably shaped to engage the cap through the socket hole 6.1.

In operation, the shaft 23 is rotated around its axis, for example in the direction of the arrow 23A. Referring to FIG. 4, the pivot link 3 is constrained to move within the slot 24. As the slot is rotated (counter-clockwise in FIG. 4) the link arm 3A, starting from an extreme right-hand position, is carried upward and to the left, to a position 3A". The link 3 carries the sleeve 8 with it, turning the sleeve on its axis A—A and moving the sleeve in the axis A—A toward one of the limits of its reciprocating motion, both at the same time. As is seen in FIG. 2, the link 3 can pivot around the pin 4 only a small angular distance when it will contact a side wall of the slot 19 of the ring 9, and then the sleeve 8 will be forced to rotate around its axis. As is seen in FIG. 1, the link 3 has no freedom to pivot around the pin 4 toward a limit of linear reciprocating motion; the sleeve 8 is immediately carried upward with the link arm 3A until a limit of linear reciprocating motion is reached. After that event, continued rotation (counterclockwise in FIG. 4) of the shaft 23 turns the slot 24 more and more into a vertical position and the link arm 3A slides along a long wall of the slot 24 while it continues to move toward the left hand side of the figure—that is, the sleeve 8 continues to rotate around its axis A—A even after reaching a limit of its linear reciprocating motion. With this construction, the limits of linear reciprocating motion can be adjusted toward or away from each other, without in any way affecting the angular oscillatory motion of the sleeve 8 around its axis A—A. When the shaft 23 has completed one-half a rotation (180°) around its axis, the link arm 3A may be in a position 3A" which represents the end of one-half cycle of the angular oscillatory motion of the sleeve. Continued rotation of the shaft 23 in the direction of the arrow 23A will bring the link arm 3A downward to a position 3A''' where the second limit of linear reciprocating motion of the sleeve 8 may be reached, after which the angular oscillatory motion is carried through to a complete cycle. Thus the sleeve 8 is carried through a combined oscillatory motion which is one of dipping in the axial direction (A—A) with simultaneous partial rotation.

If the limits of linear oscillatory motion are not established by fixed stops, as on the illustrated shoulders 5 and 33, the link arm 3A will carry the sleeve 8 to the limits of travel of the link 3 in the direction of the axis A—A. In that case, the slot 24 can be replaced with a hole that is off-set from the axial center of the face 2A by a distance which establishes the amplitude of each of the oscillations executed by the sleeve 8. It will be recognized that the slot 24 need not extend diametrically across the face 2A equally to both sides of the center; a slot extending from the center toward the periphery along a radius can also be used. Also, the slot 24 can have shapes other than the rectilinear shape that is illustrated; an elliptic shape may be useful, for example.

During rotation of the drive shaft 23 the link arm 3A moves along the slot 24 and changes the penetration into the slot as the sleeve 8 is rotated; this is illustrated by comparison of FIGS. 1 and 2, where the latter shows the link arm 3A penetrating the slot less than in FIG. 1. Clearly, these figures show the sleeve 8 at two different angular positions around its axis A—A.

We claim:

1. A tool operating apparatus for driving a tool with two oscillatory motions at substantially the same time, one of said motions being an angular oscillatory motion back-and-forth around an established axis, the other of said motions being a linear reciprocal motion back-and-forth parallel to said axis, said apparatus comprising, in combination, a tool holder having means to receive and hold a tool, housing means supporting said tool holder on said established axis with freedom to rotate around said axis and freedom to move linearly along said axis, and drive means rotatable around a second axis extending transverse to said established axis for driving said tool holder relative to said housing means with a motion having a first component that is linear reciprocal parallel to said axis and a second component that is angular back-and-forth around said axis while said drive means is in continuous unidirectional rotation around said second axis, said apparatus including means to limit the amplitude of said linear reciprocal motion independent of said angular oscillatory motion, and means to adjust said limiting means, so as to change the amplitude of said linear reciprocal motion.

2. A tool operating apparatus for driving a tool with two oscillatory motions at substantially the same time, one of said motions being an angular oscillatory motion back and forth around an established axis, the other of said motions being a linear reciprocal motion back-and-forth parallel to said axis, said apparatus comprising, in combination, a generally cylindrical tool holder having means to receive and hold a tool, housing means supporting said tool holder on said established axis with freedom to rotate around said axis and freedom to move linearly along said axis, a connecting link having a hub at one end attached to an exterior side of said tool holder on a pivot that is parallel to said axis, means adjacent said pivot to limit angular freedom of said link to move around said pivot, an arm of said link extending a distance from said pivot, and drive means rotatable around a second axis extending transverse to said established axis, said drive means engaging said arm for driving said tool holder angularly back-and-forth around said established axis and back-and-forth parallel to said established axis while said drive means is in continuous unidirectional rotation around said second axis.

3. Apparatus according to claim 2 including means to limit the amplitude of said linear reciprocal motion.

4. Apparatus according to claim 3 including means to adjust said limiting means, so as to change the amplitude of said linear reciprocal motion.

5. Apparatus according to claim 2 in which said drive means is a shaft rotatable on said second axis, said shaft having a free end face with an aperture extending through said face for receiving said arm of said link, at least a part of said aperture being radially spaced away from said second axis.

6. Apparatus according to claim 5 in which said aperture is a slot extending radially across a part of said face.

7. Apparatus according to claim 6 in which said slot extends diametrically across said face.

* * * * *